US012714734B2

(12) United States Patent
Tate

(10) Patent No.: US 12,714,734 B2
(45) **Date of Patent: *Aug. 25, 2026**

(54) TREATMENT OF PATHOGEN INFECTIONS FORMULATIONS AND METHODS FOR USE

(71) Applicant: Mitchell Lynn Tate, Surprise, AZ (US)

(72) Inventor: Mitchell Lynn Tate, Surprise, AZ (US)

(73) Assignee: Mitchell Lynn Tate, Surprise, AZ (US)

( * ) Notice: Subject to any disclaimer, the term of this patent is extended or adjusted under 35 U.S.C. 154(b) by 500 days.

This patent is subject to a terminal disclaimer.

(21) Appl. No.: 17/972,941

(22) Filed: Oct. 25, 2022

(65) Prior Publication Data

US 2024/0131100 A1 Apr. 25, 2024
US 2024/0226215 A9 Jul. 11, 2024

Related U.S. Application Data

(63) Continuation of application No. 17/184,177, filed on Feb. 24, 2021, now Pat. No. 11,583,574.

(60) Provisional application No. 63/049,030, filed on Jul. 7, 2020, provisional application No. 63/004,323, filed on Apr. 2, 2020.

(51) Int. Cl.

| | |
|---|---|
| ***A61K 36/19*** | (2006.01) |
| ***A61K 9/00*** | (2006.01) |
| ***A61K 36/752*** | (2006.01) |
| ***A61K 38/44*** | (2006.01) |
| ***A61P 31/14*** | (2006.01) |
| ***A61P 31/16*** | (2006.01) |

(52) U.S. Cl.
CPC ............ *A61K 36/19* (2013.01); *A61K 9/0053* (2013.01); *A61K 9/0078* (2013.01); *A61K 36/752* (2013.01); *A61K 38/446* (2013.01); *A61P 31/14* (2018.01); *A61P 31/16* (2018.01); *C12Y 115/01001* (2013.01)

(58) Field of Classification Search
CPC ....... A61K 36/19; A61K 38/446; A61P 31/14; A61P 31/16
See application file for complete search history.

(56) References Cited

U.S. PATENT DOCUMENTS

| | | | | |
|---|---|---|---|---|
| 5,425,944 | A | 6/1995 | Harich | |
| 9,476,051 | B2 | 10/2016 | Bennett et al. | |
| 10,806,707 | B2 | 10/2020 | Finley et al. | |
| 11,583,574 | B2 * | 2/2023 | Tate ......................... | A61K 9/08 |
| 2011/0274680 | A1 | 11/2011 | Mazed et al. | |

FOREIGN PATENT DOCUMENTS

| | | |
|---|---|---|
| CN | 101287830 | 10/2008 |
| CN | 101633916 | 1/2010 |
| HU | E02511772 | 2/2016 |
| RU | 2468809 | 12/2012 |

OTHER PUBLICATIONS

Science Based Medicine, Not Natural, not safe, grapefruit seed extract, https://sciencebasedmedicine.org/not-natural-not-safe-grapefruit-seed-extract/, Mar. 10, 2016.
Solvay Pharmaceuticals, Inc. "CREON FDA-Approved Medication Guide" 2009, p. 1-11 (Year: 2009).
Kao et al. "Direct observation of thymine dimer repair in DNA by photolyase", Nov. 8, 2005, Proceedings of the Nationals Academy of Sciences, vol. 102 No. 45, p. 16128-16132 (Year 2005).

* cited by examiner

*Primary Examiner* — Ruth A Davis
(74) *Attorney, Agent, or Firm* — Moriss O'Bryant Compagni Cannon, PLLC

(57) ABSTRACT

An oral product comprising nano-sized, heat tolerable, shelf stable peptides and enzymes. Once the peptides and enzymes are inside the body of a user, they dimerize the nucleic acids of viruses, bacteria and fungi. Thus, the peptides and enzymes are capable of inactivating the genome of pathogens, including without limitation, SARS-COV-2 and Influenza A/CA/04/2009 (H1N1) virus.

20 Claims, 4 Drawing Sheets

TREATMENT OF PATHOGEN INFECTIONS FORMULATIONS AND METHODS FOR USE

RELATED APPLICATIONS

This utility patent application is a continuation of U.S. patent application Ser. No. 17/184,177, filed Feb. 24, 2021; which claims the benefit of U.S. Provisional Patent Application Ser. No. 63,004,323, filed on Apr. 2, 2020, and U.S. Provisional Patent Application Ser. No. 63,049,030, filed on Jul. 7, 2020; all of which are hereby incorporated by reference in their entireties.

BACKGROUND

The Field of the Invention

This invention relates to oral, topical and intravenous products providing nano-sized, heat tolerable, shelf stable peptides and enzymes for inactivating various pathogens, including without limitation, viral infections such as COVID-19, or SARS-COV-2 (the causative agent of COVID-19), or Influenza A/CA/04/2009 (H1N1) virus.

Background

A wide variety of products are available for treating or addressing microbial infections and microbial contamination. An anti-microbial may be described as any agent that kills or destroys microorganisms, or stops their growth. Anti-microbials may be described based on their function. For example, an antibiotic may be used against bacteria, and an antifungal may be used against fungus, and an antiviral may be used against viruses.

The primary classes of anti-microbials include sanitizers, disinfectants, antiseptics, anti-virals, and antibiotics. Sanitizers and disinfectants may be described as non-selective agents that can kill a wide range of microorganisms on non-living surfaces, such as bleach and the like. Antiseptics may be described as non-selective and are generally applied to living tissue to clean wounds from microbes and help reduce infection. Anti-virals may be more selective and are generally used to inactivate viruses. Antibiotics may be more selective and are generally used to destroy bacteria and fungi microorganisms within the body.

Generally, anti-microbials function in two ways, chemically and physically. Anti-microbials that function chemically may include anti-bacterials, anti-fungals, anti-virals, anti-parasitics, broad-spectrum therapeutics, ozone, and non-pharmaceuticals. Anti-microbials that function physically may include heat and radiation, such as ultraviolet light.

BRIEF SUMMARY OF THE INVENTION

In accordance with the foregoing, certain embodiments of an oral and/or intravenous product and methods for production and use in accordance with the invention are described.

In one embodiment, specific plant extracts are mixed with enzyme catalysts and dissolved in alcohol, such as grain alcohol. This mixture may be added to glycerin-based grapefruit seed extract. This mixture may contain nano-sized peptide-enzyme pairing(s) or team(s). The peptide-enzyme pairing may inactivate various microbes, including without limitation, bacteria, yeasts and viruses.

In one embodiment, a method of producing an anti-microbial, anti-pathogen, solution may comprise: providing approximately two (2) grams of *Andrographis paniculata* extract; providing approximately fifteen thousand (15,000) micrograms of superoxide dismutase that is at least 900,000+ MFU per gram; dissolving at room temperature the *Andrographis paniculata* extract and the superoxide dismutase into approximately one (1) liter of 190 proof ethyl alcohol; mixing the one liter of ethyl alcohol with glycerin-based grapefruit seed extract at a ratio of approximately 1:10 by volume; and allowing the resulting mixture, or anti-microbial solution, to stand until foaming has dissipated, and the peptide-enzyme pairing has formed. The method may further comprise diluting the resulting mixture, or anti-microbial solution, into a delivery solution to an approximate level of between 0.05% and 0.5% resulting mixture, or anti-microbial solution, by volume to produce an anti-microbial product. This anti-microbial product may be pasteurized without negating the antimicrobial impact.

Moreover, the delivery solution may be comprised of a 3:1 ratio by volume of 0.9% sodium chloride in water and grape juice concentrate to produce an anti-microbial product that can be ingested by a user, or person. A user may then ingest approximately six (6) fluid ounces of this type of anti-microbial product 3-4 times a day. This results in the user's infectivity of SARS-COV-2 being reduced. The infectivity of SARS-COV-2 is reduced by a peptide-enzyme combination, or pairing, in the anti-microbial solution causing inactivation of the genome of the SARS-COV-2 microbe.

Moreover, the delivery solution may be comprised of 0.9% sodium chloride in water to produce an anti-microbial product that can be sprayed into a user's mouth, or a person's mouth, or on a surface. A user may then spray the anti-microbial product into their mouth. Each spray may be approximately one-tenth (0.1) of a mL. About 10-15 sprays can be administered in each dose. The user may spray 3-4 doses a day, with the result that the user's infectivity of SARS-COV-2 is reduced. The infectivity of SARS-COV-2 is reduced by a peptide-enzyme combination, or pairing, in the anti-microbial solution causing inactivation of the genome of the SARS-COV-2 microbe.

In one embodiment, an anti-viral solution may comprise *Andrographis paniculata* extract and superoxide dismutase dissolved in ethyl alcohol and mixed with glycerin-based grapefruit seed extract to contain a peptide-enzyme composite that is capable of inactivating the genome of SARS-COV-2. The concentration of the *Andrographis paniculata* and superoxide dismutase in the anti-viral solution may be between 0.05% and 0.5% by volume. The peptide-enzyme composite may inactivate the genome of SARS-COV-2 by dimerizing nucleic acids in the genome. The anti-viral solution may be heat tolerable and shelf-stable for approximately ten (10) years.

In one embodiment, an oral care product may provide peptides and enzymes that, once inside the body, dimerize the nucleic acids in pathogenic viruses, bacteria, and fungi. Such an oral care product can be highly effective against pathogens without toxicity issues from the use of other, related products.

BRIEF DESCRIPTION OF THE DRAWINGS

The foregoing features of the present invention will become more fully apparent from the following description and appended claims, taken in conjunction with the accompanying drawings and experimental data. Understanding that these drawings and data depict only typical embodiments of the invention and are, therefore, not to be considered limiting of its scope, the invention will be described with additional specificity and detail through use of the accompanying drawings and data in which:

DETAILED DESCRIPTION OF THE PREFERRED EMBODIMENTS

Figure 1:
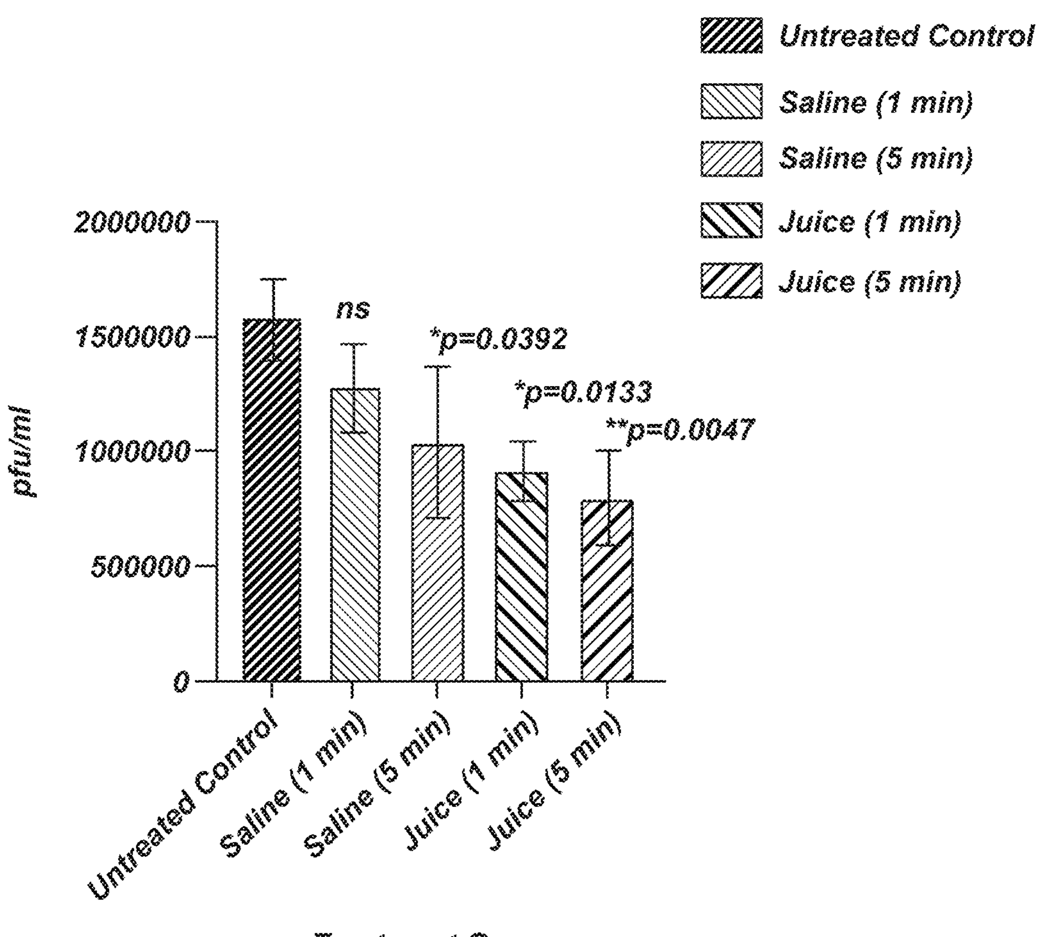
FIG. 1 illustrates results of a plaque assay analysis for SARS-COV-2 incubated in the presence of certain embodiments of the invention.

It will be readily understood that the components of the present invention, as generally described herein, could be arranged and designed in a wide variety of different configurations or formulations. Thus, the following more detailed description of the embodiments of the system, products and methods of use of the present invention, are not intended to limit the scope of the invention, as claimed, but is merely representative of various embodiments of the invention.

In one embodiment, a process for mixing specific plant extracts and enzyme catalysts, alcohol and water at room temperature is used to create an anti-microbial solution, or anti-pathogen solution, to perform, at varying dilutions and flavors, as a highly efficacious anti-pathogen, anti-viral, anti-bacterial and anti-yeast treatment inside the human body and topically on the body. This may be accomplished through a nano-sized peptide/enzyme team, or peptide-enzyme pairing, which may be the putative mechanism for causing permanent inactivation and death of pathogens, extracellularly and intracellularly, through nucleic (DNA & RNA) dimerization. This anti-microbial solution's impact is safe and non-toxic and only targets pathogens in the human body or on the human body.

The nano-sized enzymes contained in the natural plant ingredients and the nano-sized peptides contained in the natural plant ingredients and mixing these ingredients together using the natural plant enzyme catalysts, alcohol and water at room temperature, rearranges the chemical bonds of the peptides and enzymes so they bond with water in a stable, liquid water-based suspension. These bonds do not break when exposed to heat at pasteurization temperatures or when exposed to sunlight. They remain stable and suspended in the water-based liquid when salt and natural flavors are added resulting in the base, primary anti-microbial solution.

This anti-microbial solution, or anti-pathogen solution, can permanently inactivate enveloped and non-enveloped viruses, kill pathogenic bacteria, gram positive and gram negative, and kill *Candida albicans* yeast at various dilutions mixed with saline or juice. When taken orally into the human body, the amylase enzyme in the mouth breaks the peptide and enzyme bonds in the anti-microbial solution and releases them to be absorbed into the body. The bonds will also release when the liquid is in close proximity with pathogens.

The nano peptides are Cell Penetrating Peptides (CPPs) and carry the nano enzymes into the cells of the body for intracellular efficacy against invading pathogens. The nano size peptide/enzyme team, peptide-enzyme composite, can destroy the ability of microorganisms to reproduce by causing breakage or rearranging chains in nucleic acids (DNA & RNA). This interference creates specific thymine or cytosine dimers in DNA and uracil dimers in RNA, which causes permanent inactivation of microbes by causing mutations and/or cell death, and failure to reproduce or repair.

In one embodiment, an anti-microbial solution, or anti-pathogen solution, may be used in an oral product or an inhalation delivery product for the treatment of various pathogens, including but not limited to, COVID-19 viral infections. The anti-microbial solution can be utilized in various ways, including but not limited to, oral products, nebulizer products for inhalation delivery directly to the lungs, or an injection as an intravenous treatment. All of these methods of use can be utilized to treat various pathogens, including but not limited to, influenza, viral and bacterial pneumonia, common cold hepatitis, pathogen caused cancers, diabetes of pathogen origin, and secondary bacteria infections (both gram positive and gram negative), including resistant strains like MRSA and fungi like *Candida albicans* yeast. The anti-microbial solution may also be utilized topically to inactivate viruses and kill bacteria and fungi on the surface of the skin.

The anti-microbial solution may include nano-sized peptides and enzymes, which may be paired into what may be terms teams or composites or combinations. The anti-microbial solution provides these peptide-enzyme pairings or composites in a medium that is shelf-stable and heat-tolerable. The anti-microbial solution may be shelf-stable for at least ten (10) years.

The peptide-enzyme pairings or composites in the anti-microbial solution may contact pathogens and dimerize or inactivate the nucleic acids in viruses, bacteria and fungi. This process of dimerization or inactivation kills the pathogens rendering them permanently inactivated in the case of viruses, and unable to replicate and cause disease. This may account for the broad spectrum impact the anti-microbial solution has on a variety of pathogens. It may also work on tumors and cells with cancerous abnormal proliferation growth. The anti-microbial solution may also kill or inactivate the *Staphylococcus aureus* bacteria, which has been shown to cause diabetes in animals.

The peptide-enzyme pairings or composites may cause thymine base pairs next to each other in genetic sequences to bond together in pyrimidine dimers. This causes a disruption in the nucleic acid strand that reproductive enzymes cannot copy. The impact on DNA and RNA strands is to eliminate or permanently neutralize the pathogen. This process may be considered similar to how ultraviolet light, or far UV light, photons excite and alter the genome through dimerization, except that the peptide-enzyme pairings in the anti-microbial solution permanently alter the nucleic acid strands enzymatically with simultaneous anti-microbial peptide interference. Also similar to ultraviolet light, the peptide-enzyme pairings in the anti-microbial solution acts quickly and thoroughly in altering the nucleic acid strands in pathogens without harming healthy cells. The anti-microbial solution accomplishes this inside the human system, intracellularly and topically, while maintaining the safety profile.

The peptide-enzyme pairings or composites can destroy or interfere with the ability of microorganisms to reproduce by breaking or rearranging chains in nucleic acids, such as DNA and RNA. This interference creates specific thymine or cytosine dimers in DNA and uracil dimers in RNA, which causes permanent inactivation of microbes through mutations and/or cell death. The pathogen microbes are unable to reproduce and cannot repair the dimerization caused by the peptide-enzyme composites. The pathogen's built-in repair mechanisms are not able to repair the dimerizations because they cannot duplicate the new sequences. In the case of viruses, the peptide-enzyme pairing interferes with their nucleic acid code where the instructions for cell invasion and replication are coded. This causes permanent inactivation of the virus without harm to other cellular components within the body. A similar mechanism occurs with bacteria and yeasts. This is why there is a very low likelihood of resistant strains evolving against the peptide-enzyme pairings or composites. These peptide-enzyme pairings can also be utilized to enter various human cell types and intracellularly eliminate pathogens, thus treating long-term, latent infections and new symptom-revealing infections.

In one embodiment, an anti-microbial solution, or anti-pathogen solution, may be produced in the following manner. First, two (2) grams of *Andrographis paniculata* extract and fifteen thousand (15,000) international units (micrograms) of superoxide dismutase (SOD) enzyme that is a minimum of 900,000+ MFU per gram (MFU is McCord Fridovich unit, which is the international unit for SOD measurement) are allowed to fully dissolve in one (1) liter of 190 proof grain alcohol (ethyl alcohol) at room temperature. This may take approximately 20-60 minutes. Second, mix one (1) liter of the alcohol solution containing *Andrographis paniculata* extract and SOD into ten (10) liters of glycerin-based grapefruit seed extract (GSE), The grapefruit seed extract may be prepared as described in U.S. Pat. No. 5,425,944. The resulting formula ratio is 9% alcohol solution and 91% GSE. The alcohol solution and GSE are thoroughly mixed at room temperature until fully blended. This mixture is allowed to sit until any foaming has substantially reduced. Thus, the base, anti-microbial solution is produced. This method of producing the anti-microbial solution releases the nano-sized peptides and enzymes from the plant extracts and they are suspended evenly in the glycerin/alcohol medium.

The anti-microbial solution, or embodiments, may be pasteurized to sterilize and preserve them. The anti-microbial solution itself is shelf-stable, long term, and does not require pasteurization. However, when embodiment formulation requires pasteurization, the heat does not negate the anti-microbial effect, nor is the anti-microbial effect negated by exposure to sunlight. The pasteurized anti-microbial solution may be stored in any suitable, sterile container, such as HDPE plastic, glass, metal or the like. The resulting anti-microbial solution is stable, heat tolerable, and has a minimum shelf life of ten (10) years.

The anti-microbial solution may be diluted in a suitable dilution medium or solution so that the anti-microbial solution may be utilized in a variety or ways. For example, a fruit juice dilution medium or solution may be used. Similarly, a saline solution may be used as a dilution medium or solution.

In one embodiment, three (3) parts water may be mixed with one (1) part concord grape juice concentrate, or other juice concentrates or barley tea, to form a base flavoring. While any water may work, the water is preferably sterile, deionized water. This base flavoring may also include 0.9% sodium chloride mixed thoroughly with the base flavoring at room temperature. The resultant base flavoring and the anti-microbial solution may be mixed such that the concentration of anti-microbial solution is between approximately 0.05% and 0.75% anti-microbial solution. Concentrations of approximately 0.5% may be used for prescription drug oral, anti-pathogen treatments. Concentrations of approximately 0.125% may be used for inhalation delivery or over-the-counter treatments.

In one embodiment, water is the base solution. While any water may work, the water is preferably sterile, deionized water. This base solution may also include 0.9% sodium chloride mixed thoroughly with the base solution at room temperature. The resultant base solution and the anti-microbial solution may be mixed such that the concentration of anti-microbial solution is between approximately 0.05% and 0.75% anti-microbial solution. Concentrations of approximately 0.5% may be used for prescription drug oral, anti-pathogen treatments. Concentrations of approximately 0.125% may be used for inhalation delivery or over-the-counter treatments.

The anti-microbial solution, or anti-pathogen solution, may be utilized in any suitable manner to produce various delivery products, including without limitation, liquid filled soft gel capsules, hard tablets, chewable tablets, pastes, jellies, sterile spray liquid, sterile drops, or the like.

The anti-microbial solution, or anti-pathogen solution, produced in the manner described causes chemical rearranging where nano-sized enzymes rearrange the bonds of nano-sized peptides so that the nano-sized peptides and enzymes are bonded in a shelf stable, glycerin/alcohol serum or liquid. These new bonds of water/saline and the nano-sized peptides-enzymes pairings are readily released when in the mouth or stomach, and absorbed into the bloodstream.

Amylase, a digestive enzyme found in the mouth and stomach, and on the skin surface, can trigger the breaking of the bond of the nano-sized peptide-enzyme composites in the anti-microbial solution. The mere presence of pathogens may also trigger the breaking of the stable bonds and immediately release the natural peptides and enzymes, thus activating the putative mechanism.

The absorption of the nano-sized peptide-enzyme composites, or single peptides and enzymes, occurs in the mouth, stomach and upper small intestine, without reaching the lower gastrointestinal tract. Thus, the nano-sized peptide-enzyme composites, or single peptides and enzymes, do not interfere with the microbiome of the lower gut.

The peptides that contribute to the nano-sized peptide-enzyme composite include antimicrobial peptides, or AMPs. While many antimicrobial peptides disrupt membranes, some translocate into bacteria, or microorganisms, and interfere with intracellular processes. Some AMPs interact with nucleic acids. AMPs can include natural and synthetic peptides with a wide spectrum of targets, including viruses, bacteria, fungi and parasites.

Examples of Reducing Infectivity

Referring to FIG. 1, and example 1, the infectivity of SARS-COV-2, the causative agent of COVID-19, following pre-incubation for 1 or 5 minutes with various products containing an anti-microbial solution like that described herein was examined in an in vitro assay. The various products exhibited a time dependent reduction of virus infectivity in Vero cells. SARS-COV-2 incubated in the presence of one embodiment of the product for 1 or 5 minutes resulted in a 18.9% and 33.7% (p=reduction in SARS-COV-2 infectious units in the assay, respectively). SARS-COV-2 incubated in the presence of another embodiment of the product for 1 or 5 minutes resulted in a 41.1% and 48.4% reduction in infectious units in the assay, respectively.

In one embodiment, a solution containing 0.125% of an anti-microbial solution, or anti-pathogen solution, like that described herein in a saline solution was provided, which may be described as a saline anti-microbial product (or simply "Saline" as in FIG. 1), In another embodiment, a solution containing 0.5% of an anti-microbial solution, or anti-pathogen solution, like that described here in a concord grape juice solution was provided, which may be described as a juice anti-microbial product (or simply "Juice" as in FIG. 1).

SARS-COV-2 (USA-WA1/2020, NR-52281) was obtained for testing purposes. Ten microliters (10 μL) of the saline anti-microbial product or the juice anti-microbial product was combined with 10 μL of SARS-COV-2 stock virus ($10^5$ pfu/mL) or cell culture medium alone in six (6) tubes per mixture, resulting in concentrations of 0.0625% anti-microbial solution in the saline anti-microbial product samples and or 0.25% anti-microbial solution in the juice anti-microbial product samples incubated with $5\times10^4$ pfu/mL virus or medium alone. The tubes were incubated at room temperature up to five (5) minutes. Three of the tubes for each mixture were diluted with the addition of 80 μL cell culture medium at 1 minute and 5 minutes incubation.

The diluted mixtures containing 0.0125% anti-microbial solution in saline anti-microbial product or 0.05% anti-microbial solution in juice anti-microbial product and $10^4$ pfu/mL SARS-COV-2, or no virus (in test article plus medium only controls) in a volume of 100 μL were added to Vero cells in a 96-well plate and the plate was incubated for one (1) hour at 37° C. to allow for virus attachment. Following incubation, the medium was removed and replaced with fresh medium. The cells were incubated for twenty-four (24) hours at 37° C. and the supernatants were collected and used for plaque assay on Vero cells to determine the infectious units. The cells were examined visually for signs of toxicity.

The results of plaque assay analysis are presented in Table 1. Table 1 shows results of plaque assay analysis of SARS-COV-2 incubated in the presence of saline anti-microbial product or juice anti-microbial product.

TABLE 1

| | SARS-CoV-2 pfu/mL | | | | |
|---|---|---|---|---|---|
| | Replicate | | | | % |
| Treatment | 1 | 2 | 3 | Mean | Reduction |
| Untreated Control | 1750000 | 1600000 | 1400000 | 1583333 | 0.0% |
| Saline Anti-Microbial Product 1 minute | 1150000 | 1200000 | 1500000 | 1283333 | 18.9% |
| Saline Anti-Microbial Product 5 minute | 700000 | 1350000 | 1100000 | 1050000 | 33.7% |
| Juice Anti-Microbial Product 1 minute | 800000 | 950000 | 1050000 | 933333.3 | 41.7% |
| Juice Anti-Microbial Product 5 minute | 600000 | 1000000 | 850000 | 816666.7 | 48.4% |

The results of plaque assay analysis are also presented in FIG. 1. FIG. 1 shows results of plaque assay analysis for SARS-COV-2 incubated in the presence of saline anti-microbial product or juice anti-microbial product. Data were analyzed using one-way ANOVA (p values are indicated in the columns).

Both saline anti-microbial product and juice anti-microbial product exhibited a statistically significant time dependent reduction of virus infectivity in Vero cells. SARS-COV-2 incubated in the presence of 0.0625% anti-microbial solution for 1 or 5 minutes resulted in a 18.9% and 33.7% (p=reduction in SARS-COV-2 infectious units in the assay, respectively). SARS-COV-2 incubated in the presence of 0.25% anti-microbial solution for 1 or 5 minutes resulted in a 41.1% and 48.4%, reduction in infectious units in the assay, respectively. Analysis by one-way ANOVA indicated that the reductions in SARS-COV-2 infectivity resulting from incubation with 0.0625% anti-microbial solution for 5 minutes (p=0.0392), 0.25% anti-microbial solution for 1 minute (p=0.0133) or 5 minutes (p=0.0047), as indicated were all statistically significant.

With respect to toxicity, visual examination of cells incubated for one (1) hour in the diluted mixtures containing test articles and medium only indicated that there was no cellular toxicity associated with the concentrations of saline anti-microbial product or juice anti-microbial product used in the cellular assay.

In summary, this example study examined the ability of saline anti-microbial product and juice anti-microbial product to reduce the infectivity of SARS-COV-2, the causative agent of COVID-19, in a cell culture-based assay. The anti-microbial solution at concentrations of 0.0625% and 0.25% demonstrated an ability to reduce the infectivity of SARS-COV-2 when incubated with virus for 1 or 5 minutes with greater reduction at the 5 minute time point. SARS-CoV-2 infectivity was reduced by 18.9% and 33.7% following 1 minute and 5 minutes of incubation with 0.0625% anti-microbial solution, and by 41.1% and 48.4% following 1 minute and 5 minutes of incubation with 0.25% anti-microbial solution, respectively. Observation of cellular toxicity found no toxicity in cells incubated for one (1) hour with 0.0125% or 0.05% of the anti-microbial solution. The reductions in SARS-COV-2 infectivity were statistically significant.

Figure 2:
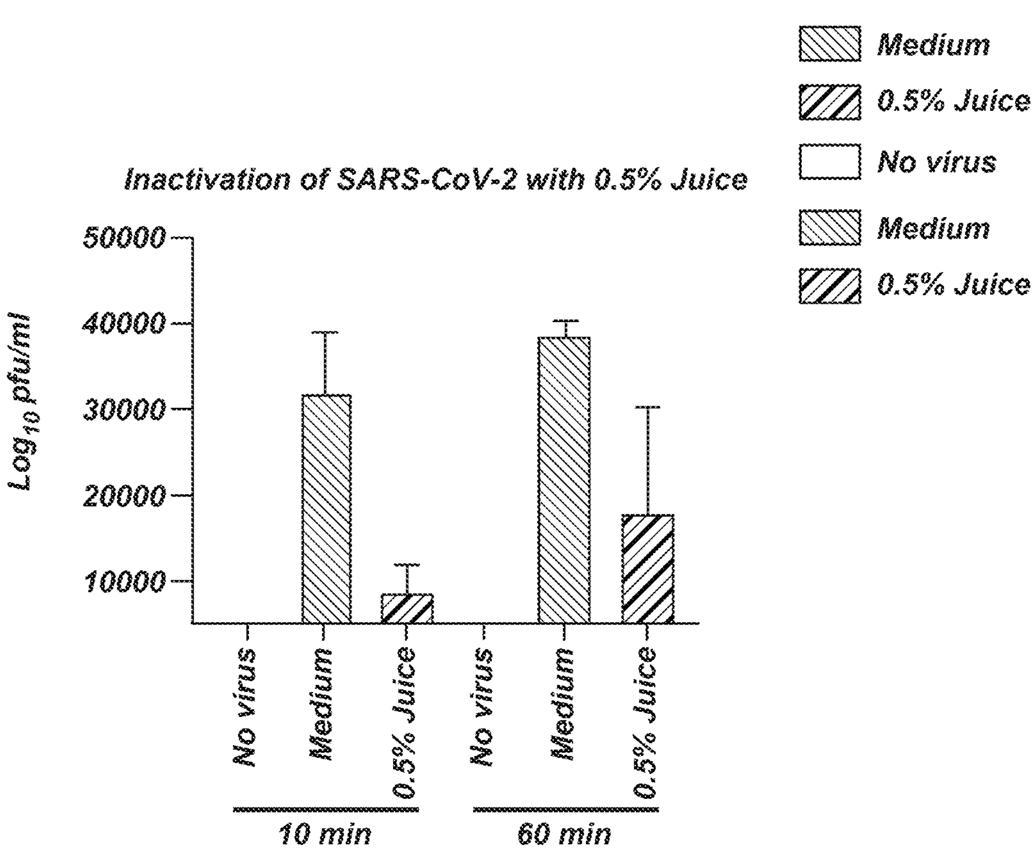
FIG. 2 illustrates results of a plaque assay analysis for SARS-COV-2 incubated in the presence of a certain embodiment of the invention.

Referring to FIG. 2, and example 2, the infectivity of SARS-COV-2, the causative agent of COVID-19, following pre-incubation for 10 or 60 minutes with a solution containing 0.5% of an anti-microbial solution, or anti-pathogen solution, like that described here in a concord grape juice solution, which may be described as a juice anti-microbial product (or simply "Juice" as in FIG. 2) was examined in an in vitro assay.

Incubation of SARS-COV-2 with the 0.5% Juice for 10 minutes at room temperature resulted in a 73.7% reduction of virus infectivity in Vero cells, compared to virus incubated in medium alone. Incubation of SARS-COV-2 with the 0.5% Juice for 60 minutes at room temperature resulted in a 54.3% reduction of virus infectivity in Vero cells, compared to virus incubated in medium alone.

The Juice product was obtained as a solution containing 1.0% of an anti-microbial solution, or anti-pathogen solution, active ingredient like that described here in concord grape juice. SARS-COV-2 (USA-WA1/2020, NR-52281) was obtained for testing purposes. Ten microliters (10 μL) of SARS-COV-2 stock virus ($10^5$ pfu/mL) was combined with ten microliters (10 μL) of the Juice anti-microbial product or cell culture medium alone in six (6) tubes per mixture, resulting in concentrations of $5\times10^4$ pfu/mL virus incubated with 0.5% Juice product or medium alone. The tubes were incubated at room temperature up to sixty (60) minutes. Three of the tubes for each mixture were diluted with the addition of 80 μL cell culture medium at 10 minutes and 60 minutes incubation.

The diluted mixtures containing $10^4$ pfu/mL SARS-COV-2 and 0.05% active ingredient Juice product, or medium in a volume of 100 μL were added to Vero cells in a 96-well plate and the plate was incubated for one (1) hour at 37° C. to allow for virus attachment. Following incubation, the medium was removed and replaced with fresh medium. The cells were incubated for twenty-four (24) hours at 37° C. and the supernatants were collected and used for plaque assay on Vero cells to determine the infectious units.

The results of plaque assay analysis are presented in Table 2. Table 2 shows results of plaque assay analysis for SARS-COV-2 incubated in the presence of medium or 0.5% Juice anti-microbial product for 10 and 60 minutes. Percent reduction is the percentage by which the viral titer was decreased relative to the medium only control at that time point.

TABLE 2

| Virus incubated with | 1 | 2 | 3 | Mean | Percent Reduction |
|---|---|---|---|---|---|
| 10 minutes (replicate) | | | | | |
| Medium only | 45000 | 20000 | 30000 | 31667 | 0.0% |
| 0.5% Juice | 5000 | 5000 | 15000 | 8333 | 73.7% |
| 60 minutes* | | | | | |
| Medium only | 40000 | 35000 | 40000 | 38333 | 0.0% |
| 0.5% Juice | 5000 | NR | 30000 | 17500 | 54.3% |

*60 minute 0.5% Juice product plaque assay replicate 2 was non-readable (NR) and replicate 3 did not display dilution-dependent quantification.

The 0.5% Juice product exhibited a reduction of virus infectivity in Vero cells at both 10 minutes and 60 minutes, Incubation of SARS-COV-2 with 0.5% Juice product for 10 or 60 minutes resulted in a reduction in infectious viral titers of 73.7% (p=0.062) and 54.3% (p=0.136), respectively.

The results of plaque assay analysis are also presented in FIG. 2. FIG. 2 shows results of plaque assay analysis for SARS-CoV-2 incubated in the presence of medium or 0.5% Juice anti-microbial product for 10 or 60 minutes. Data were analyzed using one-way ANOVA (p values are indicated in the columns). The 0.5% Juice product exhibited a reduction of virus infectivity in Vero cells at both 10 minutes and 60 minutes.

With respect to toxicity, visual examination of cells incubated for one (1) hour in the diluted mixtures containing test articles and medium only indicated that there was no cellular toxicity associated with the 0.05% concentration of Juice anti-microbial product used in the cellular assay.

In summary, this example study examined the ability of the Juice anti-microbial product to reduce the infectivity of SARS-COV-2, the causative agent of COVID-19, in a cell culture-based assay. The Juice product at a concentration of 0.5% demonstrated an ability to reduce the infectivity of SARS-COV-2 when incubated with virus for 10 or 60 minutes at room temperature. Incubation of SARS-COV-2 with 0.5% Juice product for 10 minutes resulted in a reduction in infectious viral titers of 73.7%. This is greater than previously reported for incubations of 1 and 5 minutes with 0.25% Juice product. Incubation for 60 minutes also reduced viral titers by 54.3%. The method used for analysis of viral inactivation resulted in Vero cells being exposed to mixtures containing 0.05% Juice product and $10^4$ pfu/mL SARS-COV-2, or $10^4$ pfu/mL SARS-COV-2 for one hour at 37° C. Parallel studies have indicated that 0.05% Juice product is not cytotoxic to Vero cells under these conditions, indicating that the lack of infectivity observed in the treated samples was due to inactivation of the virus by the Juice product, and not general cytotoxicity at the concentration.

Figure 3:
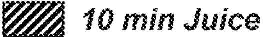
FIG. 3 illustrates results of a plaque assay analysis for Influenza A/CA/04/2009 (H1N1) incubated in the presence of a certain embodiment of the invention.
Figure 3:
Figure 3:
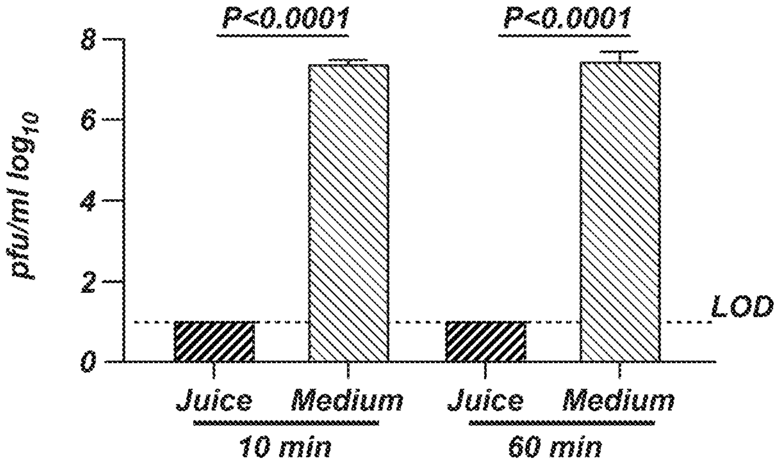

Referring to FIG. 3, and example 3, the infectivity of Influenza A/CA/04/2009 (H1N1) virus following pre-incubation for 10 or 60 minutes with a solution containing 0.5% of an anti-microbial solution, or anti-pathogen solution, like that described here in a concord grape juice solution, which may be described as a juice anti-microbial product (or simply "Juice" as in FIG. 3) was examined in an in vitro assay.

Pre-incubation Influenza A/CA/04/2009 (H1N1) virus with the 0.5% Juice for 10 minutes and 60 minutes resulted in 100% reduction of virus infectivity in MDCK cells, compared to virus incubated in medium alone.

The Juice product was obtained as a solution containing 1.0% of an anti-microbial solution, or anti-pathogen solution, active ingredient like that described here in concord grape juice. Influenza A/CA/04/2009 (H1N1) virus (NR-13658) was obtained for testing purposes and amplified in MDCK cells to produce stock virus. Ten microliters (10 μL) of stock virus ($10^5$ pfu/mL) was combined with ten microliters (10 μL) of 1.0% Juice anti-microbial product or cell culture medium alone in six (6) tubes per mixture, resulting in concentrations of $5\times10^4$ pfu/mL virus incubated with 0.5% Juice product or medium alone. The tubes were incubated at room temperature up to sixty (60) minutes. Three of the tubes for each mixture were diluted with the addition of 80 μL cell culture medium at 10 minutes and 60 minutes incubation.

The diluted mixtures containing 0.05% active ingredient Juice product and $10^4$ pfu/mL stock virus, or no virus (in test article plus medium only controls) in a volume of 100 μL were added to MDCK cells in a 96-well plate and the plate was incubated for one (1) hour at 37° C. to allow for virus attachment. Following incubation, the medium was removed and replaced with fresh medium. The cells were incubated for twenty-four (24) hours at 37° C. in an atmosphere of 5% $CO_2$, and the supernatants were collected and used for plaque assay on MDCK cells to determine the infectious units.

The results of plaque assay analysis are presented in Table 3. Table 3 shows results of plaque assay analysis for Influenza A/CA/04/2009 (H1N1) virus incubated in the presence of 0.5% Juice anti-microbial product for 10 and 60 minutes. Results are $log_{10}$-pfu/mL. N.D.=none detected/below the lower limit of detection of 10 pfu/mL.

TABLE 3

| | Influenza A log 10 pfu/mL | | | | | |
|---|---|---|---|---|---|---|
| | 10 min (replicate) | | | 60 min | | |
| Treatment | 1 | 2 | 3 | 1 | 2 | 3 |
| Medium Only | 7.431 | 7.447 | 7.477 | 7.6127 | 7.3617 | 7.5682 |
| 0.5% Juice | N.D | N.D | N.D | N.D | N.D | N.D |

The results of plaque assay analysis are also presented in FIG. 3. FIG. 3 shows results of plaque assay analysis for Influenza A/CA/04/2009 (H1N1) virus incubated in the presence of 0.5% Juice anti-microbial product for 10 or 60 minutes. Data were analyzed using one-way ANOVA (p values are indicated in the columns).

With respect to toxicity, visual examination of cells incubated for one (1) hour in the diluted mixtures containing test articles and medium only indicated that there was no cellular toxicity associated with the 0.05% concentration of Juice anti-microbial product used in the cellular assay.

In summary, this example study examined the ability of the 0.5% Juice anti-microbial product to reduce the infectivity of human pandemic influenza A virus CA/04/2009 (H1N1). Incubation of the virus with 0.5% Juice product for either 10 minutes or 60 minutes completely inactivated the ability of the virus to infect MDCK cells. Incubation for 10 minutes was sufficient to completely inactivate the virus with reductions of >6.3 $\log_{10}$ in viral titers from cells infected with the treated virus. The method used for analysis of viral inactivation resulted in MDCK cells being exposed to mixtures containing 0.05% Juice product and $10^4$ pfu/mL influenza A virus, or $10^4$ pfu/mL influenza A virus for one hour at 37° C. Visual examination of cells incubated for one hour in diluted mixtures containing test article and medium only indicated that there was no visual sign of cellular toxicity of MDCK cells with the concentration of the Juice product used in the cellular assay. This indicates that the lack of infectivity observed in the treated samples was due to inactivation of the virus by the Juice product, and not to general cytotoxicity.

Figure 4:
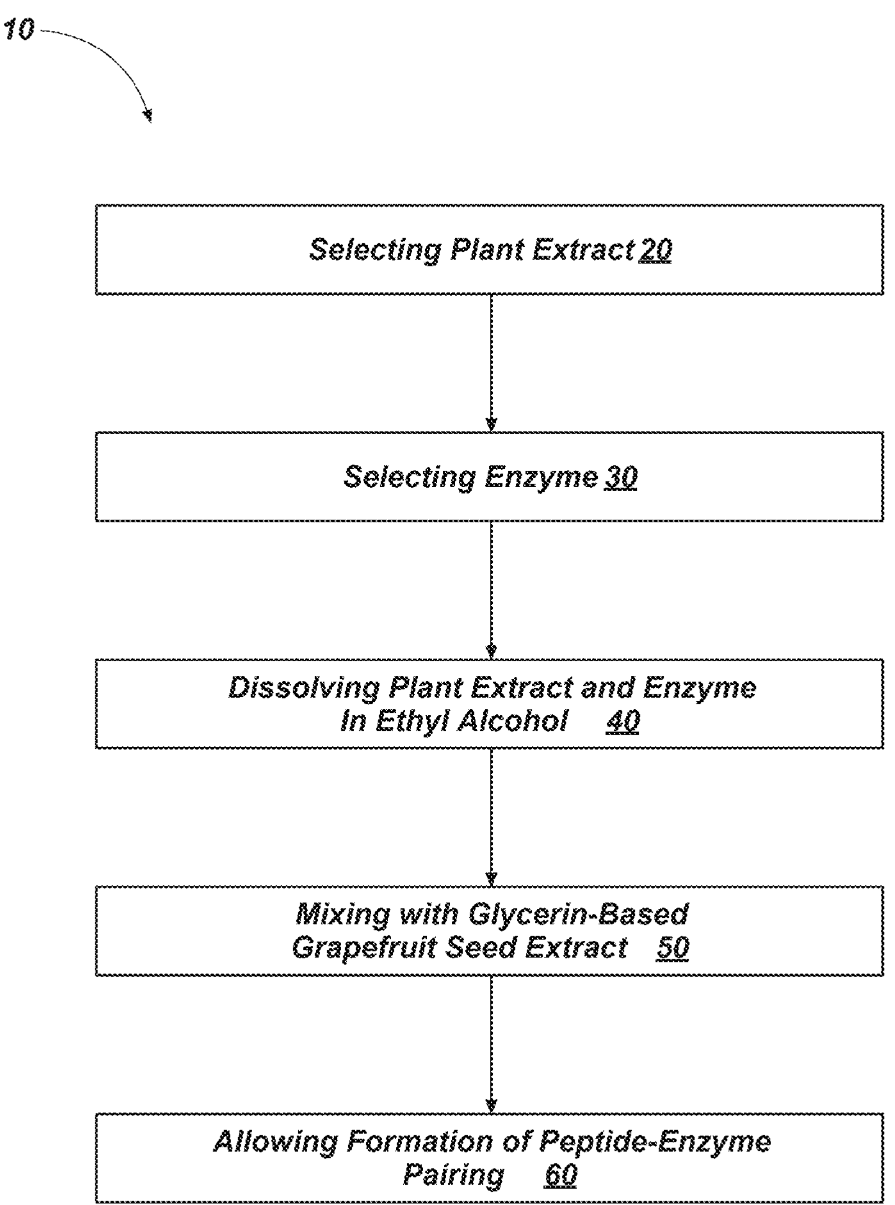
FIG. 4 illustrates a method for producing and using an anti-microbial solution to reduce infectivity of viruses, including SARS-COV-2.

Referring to FIG. 4, a method 10 for producing an anti-microbial solution, or anti-pathogen solution, using the anti-microbial solution to product an anti-microbial product, and administering the anti-microbial product to treat an infection and reduce infectivity of SARS-CoV-2, or Influenza A/CA/04/2009 (H1N1) virus, is described 10.

In one embodiment, a method of producing an anti-microbial solution may comprise multiple steps. Such a method may include selecting an appropriate plant extract 20, such as *Andrographis paniculata*, or the like. Approximately two (2) grams of *Andrographis paniculata* extract may be provided and used, but any suitable amount may be used in an appropriate ratio. Such a method may also include selecting an appropriate enzyme 30, such as superoxide dismutase, or the like. Approximately fifteen thousand (15,000) micrograms of superoxide dismutase that is at least 900,000+ MFU per gram may be provided and used, but any suitable amount may be used in an appropriate ratio.

The selected plant extract and the selected enzyme may be dissolved at room temperature into approximately one (1) liter of 190 proof ethyl alcohol (grain alcohol) 40, or the like. The ethyl alcohol solution with the plant extract and enzyme may be mixed with a glycerin-based grapefruit seed extract at a ratio of approximately 1:10 by volume 50. A suitable glycerin-based extract is described in U.S. Pat. No. 5,425,944. However, any grapefruit seed extract utilized should have all contaminants and preservatives removed prior to any mixing or use in the processes described herein. A preferred embodiment uses organic grapefruit seed, pulp, and white membranes. Moreover, the processes used and described herein may be utilized to produce an anti-microbial solution that does not contain furanocoumarins, or furocoumarins.

The resulting mixture may be allowed to stand until any foaming has significantly dissipated, and a peptide-enzyme pairing, or peptide-enzyme composite, has formed 60. This resulting mixture may be described as an anti-microbial solution, or a base solution, or a base anti-microbial solution. This anti-microbial solution may be pasteurized.

The method may further include diluting the resulting mixture, or anti-microbial solution, into a delivery solution to an approximate level of between 0.05% and 0.75% resulting mixture by volume to produce an anti-microbial product 70. This anti-microbial product may be pasteurized to sterilize and preserve the anti-microbial embodiments. This anti-microbial solution has a long, stable shelf-life and does not require pasteurization, but may be pasteurized when adding to embodiments.

In one embodiment, the delivery solution may be comprised of a 3:1 ratio by volume of 0.9% sodium chloride in water and grape juice concentrate to produce an anti-microbial product that can be ingested by a user, or person. A user may then ingest approximately six (6) fluid ounces of the anti-microbial product 3-4 times a day. This results in the user's infectivity of SARS-COV-2 being reduced. The infectivity of SARS-COV-2 is reduced by a peptide-enzyme combination, or pairing, in the anti-microbial solution causing inactivation of the genome of the SARS-COV-2 microbe.

In one embodiment, the delivery solution is comprised of 0.9% sodium chloride in water to produce an anti-microbial product that can be sprayed into a user's mouth, or a person's mouth, or on a surface. A user may spray the anti-microbial solution into their mouth. Each spray may be approximately one-tenth (0.1) of a mL. About 10-15 sprays can be administered in each dose. The user may spray 3-4 doses a day, with the result that the user's infectivity of SARS-COV-2 is reduced. The infectivity of SARS-COV-2 is reduced by a peptide-enzyme combination, or pairing, in the anti-microbial solution causing inactivation of the genome of the SARS-COV-2 microbe.

In one embodiment, an anti-viral solution may comprise *Andrographis paniculata* extract and superoxide dismutase dissolved in ethyl alcohol and mixed with glycerin-based grapefruit seed extract to contain a peptide-enzyme composite that is capable of inactivating the genome of SARS-COV-2. The concentration of the *Andrographis paniculata* and superoxide dismutase in the anti-viral solution may be between 0.05% and 0.5% by volume. The peptide-enzyme composite may inactivate the genome of SARS-COV-2 by dimerizing nucleic acids in the genome. The anti-viral solution may be heat tolerable and shelf-stable for approximately ten (10) years.

In one embodiment, a regimen of treating a microbial infection may include administering the juice anti-microbial product 80 to alleviate symptoms and reduce infectivity of SARS-COV-2, or Influenza A/CA/04/2009 (H1N1) virus 90. For example, the juice anti-microbial product may contain approximately 0.5% anti-microbial solution by volume. For an adult with an acute infection, a recommended dosage may be to drink 6 ounces 3-4 times a day (every 4 hours) until symptoms subside. As symptoms are relieved, continue to drink 6 ounces twice a day for 5 days after symptoms have dissipated. Then, drink 4 ounces twice a day for 7 days. For prevention, an adult may drink two ounces a day. For children under 100 pounds, 12-15 drops (¼ teaspoon, or 1 mL) may be administered every 3-4 hours until symptoms subside. For toddlers and under two years old, 5-8 drops (0.5 mL) may be administered every 3-4 hours until symptoms subside.

In one embodiment, a regimen of treatment may include administering the saline anti-microbial product 80 to alleviate symptoms and reduce infectivity of SARS-COV-2 90. For example, the saline anti-microbial product may contain approximately 0.125% anti-microbial solution by volume. For an adult with an acute infection, 10-15 sprays may be applied orally inside the mouth every 3-4 hours until symptoms subside. Allowing approximately 60 seconds of exposure in the mouth before swallowing can maximize efficacy. For children under 100 pounds, 3-5 sprays may be applied orally inside the mouth every 3-4 hours until symptoms subside. For toddlers and under two years old, 1-3 sprays may be applied orally inside the mouth every 3-4 hours until symptoms subside.

A nebulizer may also be utilized to administer the saline anti-microbial product via inhalation 80. The saline anti-microbial product may be poured into the liquid tray of a nebulizer and turning on the nebulizer unit. A breathing treatment may be administered by having the person breathe deeply for 30 seconds and relax for 15 seconds, repeating this cycle five times. This breathing treatment may be administered 3-4 times a day until symptoms subside 90.

In one embodiment, a regimen of treatment may include utilizing both a saline anti-microbial product and a juice anti-microbial product 80. For example, the saline anti-microbial product may contain approximately 0.125% anti-microbial solution by volume and the juice anti-microbial product may contain approximately 0.5% anti-microbial solution by volume.

The early use of such a regimen can be very helpful in any treatment plan. The earlier in an illness cycle this regimen is used can result in faster relief of illness symptoms. If a person or user presents with viral and/or secondary bacterial infection, and are in the later or final stages of a disease, an increased dosage of the saline anti-microbial product and the juice anti-microbial product may be recommended for a 48-hour time period to arrest viral and bacterial growth. The impact of the regimen is dose related, so keeping the respective products in the body system can help reduce the number of days of sickness and promote earlier relief of symptoms. This regimen may be used as a treatment of SARS-COV-2 to reduce infectivity 90.

The saline anti-microbial product may be administered via inhalation. For persons or users in an advanced stage of COVID-19, or with an acute, serious infection, such an inhalation or nebulizer additional treatment may be considerably helpful, even essential. Any SARS-COV-2 present in an airway can be directly inactivated and prevent implementation of the hypoxia portion of an infection. Such a combined use of the saline anti-microbial product and the juice anti-microbial product can effectively stop the hypoxia and permanently inactivate the virus. In the body, a bacterial component of an infection can react differently than a viral component. Thus, using both the saline anti-microbial product via inhalation and the juice anti-microbial product is most beneficial and effective.

In one embodiment, an alternating combination of a juice anti-microbial product and a saline anti-microbial product may used to treat a microbial infection. Methods and dosages may be used as described herein.

Similarly, an alternating combination of methods for administering a saline anti-microbial product may be used. For example, and not by way of limitation, a saline anti-microbial product may be administered orally, by spraying, and by inhalation, via a nebulizer. Thus, a saline anti-microbial product may be administered orally and then by inhalation, alternating methods of administration, to treat a microbial infection, even to reduce infectivity of SARS-COV-2.

The subject invention may be more easily comprehended by reference to the specific embodiments recited herein, which are representative of the invention. However, it must be understood that the specific embodiments are provided only for the purpose of illustration, and that the invention may be practiced in a manner separate from what is specifically illustrated without departing from its scope and spirit.

What is claimed and desired to be secured by United States Letters Patent is:

1. A method for treating a viral infection, comprising:

providing approximately two (2) grams of *Andrographis paniculata* extract;

providing approximately fifteen thousand (15,000) micrograms of superoxide dismutase that is at least 900,000+ MFU per gram;

dissolving at room temperature the *Andrographis paniculata* extract and the superoxide dismutase into approximately one (1) liter of 190 proof ethyl alcohol;

mixing the one liter of ethyl alcohol with glycerin-based grapefruit seed extract at a ratio of approximately 1:10 by volume;

allowing the resulting mixture, an anti-microbial solution, to stand until foaming has dissipated;

providing a juice solution comprised of a 3:1 ratio by volume of 0.9% sodium chloride in water and juice concentrate;

diluting the anti-microbial solution into the juice solution to a level of between 0.05% and 0.75% anti-microbial solution by volume to produce a juice anti-viral product; and ingesting, by a user, approximately six (6) fluid ounces of the juice anti-viral product 3-4 times a day.

2. The method of claim 1, further comprising:

providing a dilution solution comprised of 0.9% sodium chloride in water;

diluting the anti-microbial solution into the dilution solution to a level of between 0.05% and 0.5% anti-microbial solution by volume to produce a saline anti-viral product; and administering, via a nebulizer by inhalation to the user, the saline anti-viral product, wherein the user breathes deeply for approximately 30 seconds and relaxes for approximately 15 seconds, and repeats this cycle five times in a dosing.

3. The method of claim 2, further comprising:

pasteurizing the juice anti-viral product before ingestion; and pasteurizing the saline anti-viral product before use in the nebulizer.

4. The method of claim 3, further comprising forming a peptide-enzyme combination in the anti-microbial solution that causes inactivation of the genome of a SARS-COV-2 microbe.

5. The method of claim 2, wherein the saline anti-viral product is approximately 0.125% anti-microbial solution by volume.

6. The method of claim 1, further comprising:

providing a dilution solution comprised of 0.9% sodium chloride in water;

diluting the anti-microbial solution into the dilution solution to a level of between 0.05% and 0.5% anti-microbial solution by volume to produce a saline anti-viral product; and spraying the saline anti-viral product into the mouth of the user, wherein each spray is approximately one-tenth (0.1) of a mL and about 10-15 sprays are administered in each dose and the user sprays 3-4 doses a day.

7. The method of claim 6, further comprising forming a peptide-enzyme combination in the anti-microbial solution that causes inactivation of the genome of a SARS-COV-2 microbe.

8. The method of claim 6, wherein the saline anti-viral product is approximately 0.125% anti-microbial solution by volume.

9. The method of claim 1, wherein the juice anti-viral product is approximately 0.5% anti-microbial solution by volume.

10. A method for producing an anti-pathogen solution, comprising:
providing approximately two (2) grams of *Andrographis paniculata* extract;
providing approximately fifteen thousand (15,000) micrograms of superoxide dismutase that is at least 900,000+ MFU per gram;
dissolving at room temperature the *Andrographis paniculata* extract and the superoxide dismutase into approximately one (1) liter of 190 proof ethyl alcohol;
mixing the one liter of ethyl alcohol with glycerin-based grapefruit seed extract at a ratio of approximately 1:10 by volume; and
allowing the resulting mixture, the anti-pathogen solution, to stand until foaming has dissipated and a peptide-enzyme composite has formed.

11. The method of claim 10, further comprising:
providing a juice solution comprised of a 3:1 ratio by volume of 0.9% sodium chloride in water and juice concentrate;
diluting the anti-pathogen solution into the juice solution to a level of between 0.05% and 0.75% anti-microbial solution by volume to produce a juice anti-pathogen product;
ingesting, by a user, approximately six (6) fluid ounces of the juice anti-pathogen product 3-4 times a day; and
inactivating the genome of at least one of the pathogens selected from the group consisting of: SARS-COV-2, Influenza A (H1N1), Gram Positive Bacteria, Gram Negative Bacteria, yeast, and fungi.

12. The method of claim 11, wherein the inactivating the genome of the pathogens reduces the infectivity of the pathogens by the peptide-enzyme composite dimerizing nucleic acids in the genome of the pathogens.

13. The method of claim 11, further comprising:
pasteurizing the juice anti-pathogen product before the ingesting by the user.

14. The method of claim 10, further comprising:
providing a dilution solution comprised of 0.9% sodium chloride in water;
diluting the anti-pathogen solution into the dilution solution to a level of between 0.05% and 0.5% anti-pathogen solution by volume to produce a saline anti-pathogen product;
spraying the saline anti-pathogen product into the mouth of a user, wherein each spray is approximately one-tenth (0.1) of a mL and about 10-15 sprays are administered in each dose and the user sprays 3-4 doses a day; and
inactivating the genome of at least one of the pathogens selected from the group consisting of: SARS-COV-2, Influenza A (H1N1), Gram Positive Bacteria, Gram Negative Bacteria, yeast, and fungi.

15. The method of claim 14, wherein the inactivating the genome of the pathogens reduces the infectivity of the pathogens by the peptide-enzyme composite dimerizing nucleic acids in the genome of the pathogens.

16. A method for producing an anti-pathogen solution, comprising:
providing approximately two (2) grams of *Andrographis paniculata* extract;
providing approximately fifteen thousand (15,000) micrograms of superoxide dismutase that is at least 900,000+ MFU per gram;
dissolving at room temperature the *Andrographis paniculata* extract and the superoxide dismutase into approximately one (1) liter of 190 proof ethyl alcohol;
mixing the one liter of ethyl alcohol with glycerin-based grapefruit seed extract at a ratio of approximately 1:10 by volume;
allowing the resulting mixture, the anti-pathogen solution, to stand until foaming has dissipated and a peptide-enzyme composite has formed, wherein the peptide-enzyme composite is nano-sized; and
pasteurizing the anti-pathogen solution.

17. The method of claim 16, further comprising:
providing a juice solution comprised of a 3:1 ratio by volume of 0.9% sodium chloride in water and juice concentrate; and
diluting the anti-pathogen solution into the juice solution to a level of between 0.05% and 0.75% anti-microbial solution by volume to produce a juice anti-pathogen product.

18. The method of claim 17, further comprising:
ingesting, by a user, the juice anti-pathogen product; and
inactivating the genome of at least one of the pathogens selected from the group consisting of: SARS-COV-2, Influenza A (H1N1), Gram Positive Bacteria, Gram Negative Bacteria, yeast, and fungi.

19. The method of claim 16, further comprising:
providing a dilution solution comprised of 0.9% sodium chloride in water;
diluting the anti-pathogen solution into the dilution solution to a level of between 0.05% and 0.5% anti-pathogen solution by volume to produce a saline anti-pathogen product.

20. The method of claim 19, further comprising:
spraying the saline anti-pathogen product into the mouth of a user; and
inactivating the genome of at least one of the pathogens selected from the group consisting of: SARS-COV-2, Influenza A (H1N1), Gram Positive Bacteria, Gram Negative Bacteria, yeast, and fungi.

* * * * *